(12) United States Patent
Lai

(10) Patent No.: US 6,231,566 B1
(45) Date of Patent: *May 15, 2001

(54) METHOD FOR SCANNING A PULSED LASER BEAM FOR SURFACE ABLATION

(75) Inventor: Ming Lai, Dublin, CA (US)

(73) Assignee: Katana Research, Inc., Pleasanton, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/371,968

(22) Filed: Aug. 10, 1999

Related U.S. Application Data

(60) Provisional application No. 60/096,282, filed on Aug. 12, 1998.

(51) Int. Cl.[7] ................................................ A61B 18/18
(52) U.S. Cl. ................................ 606/5; 606/2; 606/10; 606/17; 219/121.8
(58) Field of Search ................................ 606/2, 3–6, 10, 606/17, 18; 219/121.6, 121.73, 121.74, 121.75, 121.79, 121.8

(56) References Cited

U.S. PATENT DOCUMENTS

| | | |
|---|---|---|
| 4,665,913 | 5/1987 | L'Esperance, Jr. . |
| 4,718,418 | 1/1988 | L'Esperance, Jr. . |
| 5,284,477 * | 2/1994 | Hanna et al. ............................. 606/5 |
| 5,520,679 | 5/1996 | Lin . |
| 5,599,340 | 2/1997 | Simon et al. . |
| 5,618,285 | 4/1997 | Zair . |
| 5,634,920 | 6/1997 | Hohla . |
| 5,743,902 * | 4/1998 | Trost ...................................... 606/18 |
| 5,782,822 | 7/1998 | Telfair et al. . |
| 5,971,978 * | 10/1999 | Mukai .................................... 606/18 |
| 6,010,497 * | 1/2000 | Tang et al. ............................... 606/5 |

* cited by examiner

Primary Examiner—Lee Cohen
Assistant Examiner—Ahmed Farah
(74) Attorney, Agent, or Firm—Fish & Richardson P.C.

(57) ABSTRACT

A fast and smooth scanning for achieving a uniform ablated surface without relying on any synchronization between the laser pulses and the scanner mirror positions. The scanning takes a series of close loops and the scanning speed on each loop is fine-tuned according to the perimeter of the loop. A uniform and close-packed pulse disposition along each loop can be achieved by multiple successive scans along the loop, while the consecutive pulses of a scan can be well separated. The scanning pattern is designed such that the energy distribution is uniform for every layer and the smoothness of the ablated surface remains substantially unchanged as the number of the layer increases.

21 Claims, 5 Drawing Sheets

METHOD FOR SCANNING A PULSED LASER BEAM FOR SURFACE ABLATION

This application claims the benefit of U.S. provisional application No. 60/096,282, filed on Aug. 12, 1998.

FIELD OF THE INVENTION

The present invention relates to scan a pulsed laser beam for surface ablation. In particular, the present invention relates to scan a pulsed laser beam of high repetition rate and small spot size to achieve smooth and uniform ablation.

BACKGROUND OF THE INVENTION

To achieve smooth and uniform surface ablation with a pulsed laser beam of high repetition rate and small spot size, a fast and smooth scanning and a proper scanning pattern are crucial. When an intense UV laser pulse impinges a corneal surface, for instance, a plume of decomposed tissue is ejected from the surface. This ejected material may affect the energy disposition of the next pulse. Besides, the stress and heat generated from the ablation process may build up if the pulsed laser beam is not scanned fast enough. Each pulse creates an ablated pit having a typical depth of a fraction of a micron. A uniform ablation profile can be expected only when these pits are arranged in a proper disposition pattern.

There are some 500 U.S. patents associated to scanning a laser beam. The present invention relates specifically to scan a pulsed laser beam for surface ablation. In particular, the present invention relates to scan a pulsed laser beam with a high repetition rate (about a kilohertz) and a small spot size (a fraction of a millimeter) for smooth and uniform surface ablation. A direct application of the present invention is to scan a pulsed laser beam for photo-refractive surgery on a cornea to correct vision disorders.

A few scanning methods have been proposed for photo-refractive surgery. In U.S. Pat. Nos. 4,665,913 and 4,718,418, L'Esperance Jr. presented a method to scan laser pulses with a uniform power over a squared cross section. The scanner is synchronized with the pulses to achieve precise disposition of the pulses. Lin demonstrated in U.S. Pat. No. 5,520,679 a method to achieve smooth ablation by accurately controlling the beam spot size and carefully overlapping the pulses in a single layer. A 100 Hz-pulsed UV laser beam was scanned linearly to show a desirable result. Simon and Wuang disclosed in U.S. Pat. No. 5,599,340 a method of disposing the laser pulses over a programmed pattern in a random process. For a pulsed laser of low repetition rate, this programmed random process can generate a similar result as that of continuous scanning.

When the pulse repetition rate is increased to the kilohertz level, however, the above mentioned scanning methods become non-practical. At a kilohertz repetition rate, the time interval between the pulses is only a millisecond. This is too fast for today's scanner to synchronize precisely the scanner mirror position with the laser pulses. Uniform disposition of the pulses becomes impossible with linear scanning because of the slowdown of the scanning when the beam turns around. Close overlapping between the pulses is not desirable because the plume from the previous pulse will affect the energy disposition of the next pulse. Besides, an accurate spot size on the target is practically impossible to defined and to maintain when the pulse energy varies with time.

SUMMARY OF THE INVENTION

The present invention contemplates a fast and smooth scanning so that the consecutive pulses in each pass of scanning are well separated and uniformly disposed. The scanning does not rely on any synchronization between the laser pulses and the scanner mirror positions. Instead, the scanning takes a series of close loops and the scanning speed on each loop is fine-tuned according to the perimeter of the loop. A uniform and close pulse disposition along the loop is achieved by multiple successive scans along the loop. The scanning pattern is designed such that the energy distribution is uniform for every layer and the smoothness of the ablated surface remains an acceptable level as the number of the layers increases.

In a preferable embodiment, the scanning takes a pattern of concentric rings in each layer. The laser beam is scanned from one ring to another in a spiral fashion. The scanning is approximately at a constant speed, which is set according to the pulse repetition rate and a predetermined disposition space between consecutive pulses. The scanning speed is then fine tuned for each individual ring according to the perimeter of the ring so that the pulse disposition can be uniformly filled in each ring precisely. The pulse disposition on each ring can be accomplished in one or more successive scans along the ring. The scanning deposits the pulses along one ring at a time and then swings smoothly from ring to ring and from layer to layer.

The scanning is spirally inward and outward alternately to generate multiple layers. The diameters of the rings are uniformly increased or decreased in each layer and are slightly varied from layer to layer. Thus, a controllable average can be obtained over the layers and the roughness of the energy disposition will not be built up as the number of layer increases. In the case of UV photo-refractive surgery, the ablation depth of each layer is typically a fraction of a micron and the surface is expected to remain rather smooth after many layers of ablation.

Accordingly, an objective of the present invention is to provide a new and improved method for scanning a pulsed laser beam of high repetition rate and small spot size to achieve a smooth scanning and a uniform ablation.

Another objective of the present invention is to provide a new and improved method to eliminate the effect of the ablation plume on the energy disposition of a pulsed laser beam of high repetition rate.

A further objective of the present invention is to provide a new and improved method to obtain uniform ablation without the synchronization between the laser pulses and the scanner mirror positions.

Another further objective of the present invention is to provide a new and improved method to conduct photo-refractive surgeries with a deep UV laser beam of high repetition rate and small spot size.

These and other objectives and advantages of the invention will become more apparent in the following drawings, detailed description and claims.

BRIEF DESCRIPTION OF THE DRAWINGS

FIG. 2 shows possible patterns of prior art scanning when synchronization is not achievable.

DETAILED DESCRIPTION OF A PREFERRED EMBODIMENT

Figure 1:
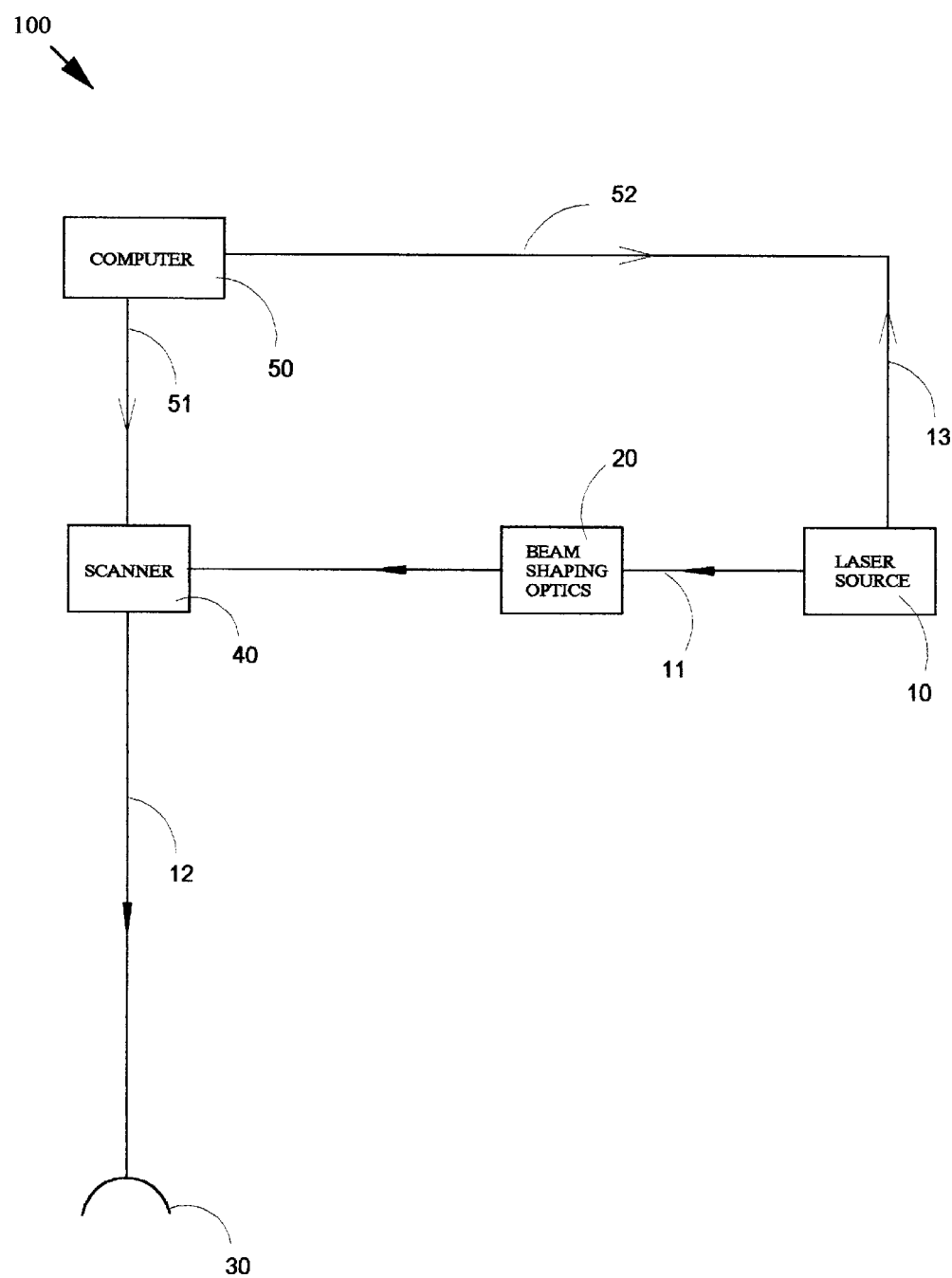
FIG. 1 is a schematic diagram showing a typical layout for surface ablation with a scanning laser beam.

FIG. 1 is a schematic diagram showing an ablation system 100, as one embodiment of the present invention. The ablation system 100 consists of a laser source 10, a beam shaping optics 20, a scanner 40, and a computer 50. The system 100 produces a scanning laser beam 12 to ablate on a target 30.

The laser source 10 produces a pulsed laser beam 11. The laser beam 11 has a predetermined wavelength, pulse energy, pulse duration, and pulse repetition rate. The wavelength can be within the spectral range from ultraviolet to infrared. For a photo-refractive surgery, the wavelength should be in the deep UV spectrum ranging from 220 nm to 180 nm or in the infrared spectrum near 3 micron. The pulse energy is in the range from 10 uJ to 1000 uJ. The pulse duration is in the range from 0.01 ns to 100 ns. The repetition rate is in the range from 0.2 kHz to 10 kHz.

The beam shaping optical assembly 20 controls the spot size of the laser beam 12 on the target 30 to obtain a proper energy density and a desirable ablation rate. The spot size, depending on the pulse energy, should be in the range of 50–1000 microns.

The two-dimensional scanner 40 receives the pulsed laser beam 11 and projects it as beam 12 onto the target 30. The scanner 40 has a fast response to the input signal 51, up to a kilohertz. The scanner 40 can be a pair of Galvanometers.

The computer 50 interfaced with the scanner 40 generates a programmable signal 51 to control the scanning of the scanner 40. The computer 50 is also interfaced with the laser source 10 to read in or control the repetition rate of the laser beam 11. The communication between the computer 50 and the laser source 10 is accomplished through a source signal 13 and a control signal 52.

When the repetition rate of the pulsed laser beam 11 is up to a kilohertz, the time interval between the pulses is only a millisecond. This time interval is too short for many existing commercial scanners to synchronize the scanner mirror position with the laser pulses. To achieve uniform disposition of the laser pulses, continuous and smooth scanning is essential. Linear scanning is no longer suitable due to its sharp stop and turnaround at the ends. As a preferred embodiment, circular and spiral scanning is presented in the following discussion.

Figure 2A:
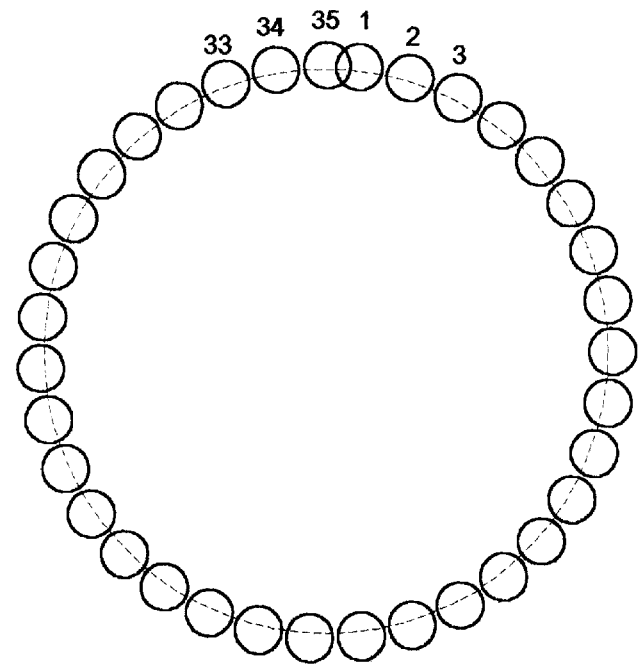
FIG. 2a shows a closely packed scanning and FIG. 2b shows a double pass scanning.

FIG. 2 shows possible patterns of prior art scanning when synchronization is not achievable. A closely packed scanning is used in FIG. 2a, which can produce a uniform pulse disposition along a ring but may have an interrupt of the uniformity at the joint point. As illustrated in the FIG. 2a, the spot of the first pulse is labeled number 1 and the last pulse labeled number 35. This type of scanning is slow and is not favorable for surface ablation with high repetition pulses. When an intense UV laser pulse impinges on a corneal surface, for example, a plume of decomposed tissue is ejected from the surface. This ejected material may affect the energy disposition of the next pulse. A fast scanning to separate the consecutive pulses on the ablated surface is an important measure for achieving uniform and predictable energy disposition.

Figure 2B:
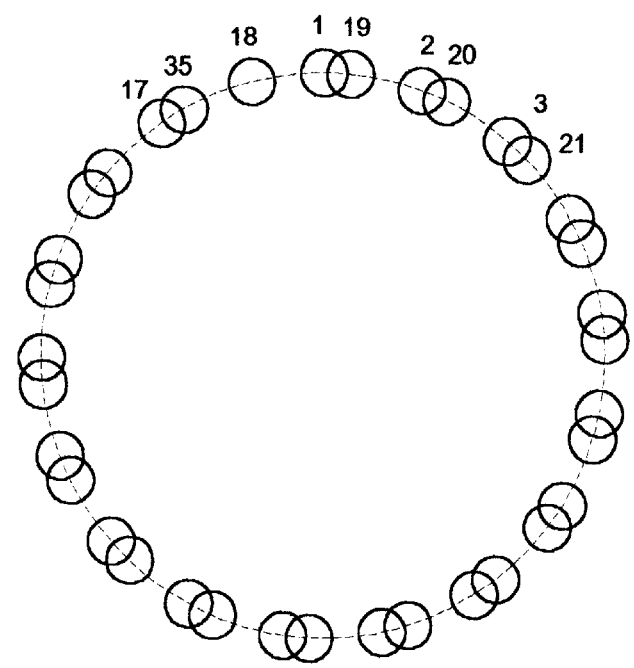

FIG. 2b shows a double pass scanning along a ring with large reparation between consecutive pulses. This scanning does not usually lead to a uniform disposition of the pulses, as illustrated in the FIG. 2b. The spots of the first scan labeled as 1 through 18 are partially overlapped by the spots of the second scan labeled as 19 through 35. Although a large number of scans will give a result of random average, the pulses may form clusters and a rough ablated surface may occur.

Figure 3:
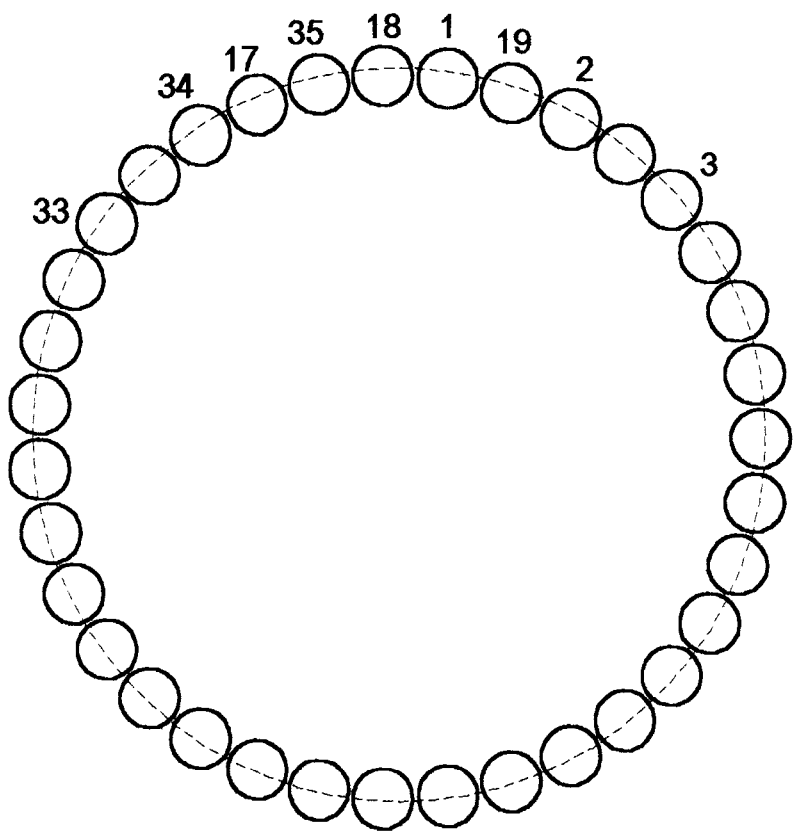
FIG. 3 shows a uniform disposition of the laser pulses along a ring by two successive scans in accordance with the present invention.

FIG. 3 shows a uniform disposition of the laser pulses along a ring by two successive scans, as one embodiment in accordance with the present invention. Here, the scanning speed is fine-tuned according to the ring perimeter and the pulse repetition rate. As depicted in FIG. 3, the separation between consecutive pulses is about twice the size of the pulse spot, and the ring perimeter is filled uniformly and precisely by the pulses disposed in two successive scans. There is no interrupt of the uniformity at the joint point.

To achieve a result similar to that of FIG. 3, the computer 50 should be programmed to perform the following. First, calculate the perimeter P of a ring R to be scanned on the target 30. Second, divide P by a predetermined approximate separation D between consecutive pulses on the target 30. Third, round off P/D to obtain an integer n, which equals to the number of pulses that can be fitted into the ring perimeter in each single scan. Fourth, calculate the precise separation $D'$ between consecutive pulses along the ring R by the formula:

$$D'=mP/(nm+1), \quad (1)$$

where m is an integer equal to the number of scans to go around ring R. Fifth, determine the scanning speed V by multiplying the separation $D'$ and the repetition rate K. That is:

$$V=KD'=mPK/(nm+1). \quad (2)$$

Then, the computer 50 can send a driven signal 51 to the scanner 40 to scan the beam 12 at a speed V along the ring R. With such a scanning speed V, the separation $D'$ is warranted and thus the relation $D'=mP/(nm+1)$ is satisfied. This way, a number of $nm+1$ pulses will be disposed uniformly and precisely onto the ring R by m successive scans.

For the example of FIG. 3, we have m=2, n=17, and the spot size of the pulses is about D/2. There are a total of 35 spots on the ring. The pulse disposition starts from spot 1, goes to spot 2, and ends at spot 18 for the first scan. As the scan continues to the second round, spot 19 fills in between spot 1 and spot 2, and so on. The exact position of spot 1 along the ring is not controllable due to the lack of synchronization between the scanner mirror position and the pulses. The pattern of the pulse disposition is, however, programmable and uniform with the scanning scheme of the present invention.

It is important to note that only the scanning speed V is fine-tuned and there is no requirement to synchronize the scanner mirror position with the laser pulses. It is also important to note that the separation $D'$ between the consecutive pulses can be m times bigger than the actual pulse disposed along the ring.

Actually, the scanning speed V varies only slightly from ring to ring to satisfy the above equation (2), because $D'$ differs from D by typically only a small fraction. For instance, assuming an approximate separation D=1 mm and a constant pulse repetition rate K=1 kHz, an approximate scanning speed is then 1 m/s on the target. Further assuming for FIG. 3 a ring of 2R=5.5 mm, we have P=2 $\pi$R=17.3 mm and n=17. With m=2 in equation (2), we thus have $D'$=0.99 mm and V=0.99 m/s.

According to equation (2), the scanning speed V can be kept constant if the repetition rate K is to be fine-tuned. Similar result can be obtained. However, fine tuning of the scanning speed V is preferable because it is easier to achieve than fine tuning of the repetition rate K in a time interval of a millisecond.

Figure 4:
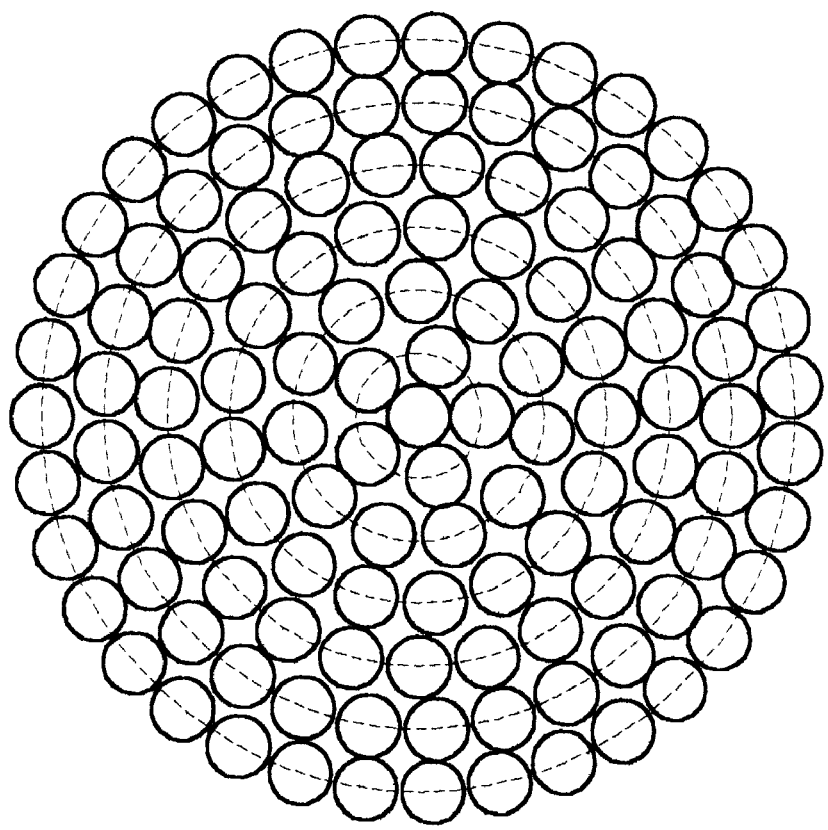
FIG. 4 shows a uniform disposition of the laser pulses on a layer of concentric rings, each of which is formed by two successive scans.

FIG. 4 shows a uniform disposition of the laser pulses on a layer of concentric rings, each of which is formed by two successive scans. The pulsed laser beam is scanned two cycles along each ring and then switched to next ring. Therefore, the scanning looks like in a spiral fashion, either spiral inward or spiral outward.

Figure 5:
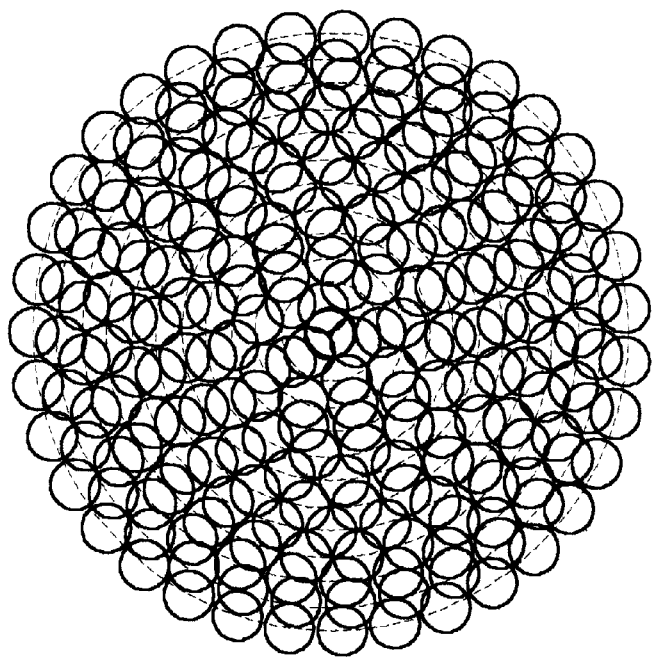
FIG. 5 shows a uniform disposition of the laser pulses on two overlapped layers of concentric rings, the rings on the second layer are located on top and between the rings on the first layer.

FIG. 5 shows a uniform disposition of the laser pulses on two overlapped layers of concentric rings; the rings on the second layer are located on top and between the rings on the first layer. To form this disposition, two layers of FIG. 4 are scanned, one is spiral inward and the other is spiral outward. In this arrangement, the radial valleys and peaks of the second layer are aligned with the radial peaks and valleys of the first layer. Thus, the radial smoothness of the two-layer's ablation is improved over that of one-layer's ablation.

To stack more layers on each other, the pulsed laser beam can be scanned layer by layer, spiral inward and outward alternately. The sizes of the rings on different layers can be adjusted such that an average can be taken over the layers along radial direction. Thus, the pulse disposition is uniform on each layer and the radial average over the layers is controllable. Consequently, the roughness of the ablated surface will not be built up significantly as the number of layer increases. In the case of UV photo-refractive surgery, the ablation depth of each layer is typically a fraction of a micron and the surface is expected to remain rather smooth after many layers of ablation.

One scheme for achieving good radial average over the layers is to treat as a group every two layers shown in FIG. 5 and to vary the sizes of the rings from group to group. The following is an example.

Assume the radii of the rings on the first layer as: $r_1=r_0+j\delta$, where $r_0$ is a constant, $\delta$ is the increment between two neighboring rings, and j is an integer. The radii of the rings on the second layer are then given by: $r_2=r_1+\delta/2$. One set of radii for the progressive layers can thus be chosen as:

$r_1=r_0+j\delta$,
$r_2=r_1+\delta/2$;
$r_3=r_1+\delta/4$,
$r_4=r_2+\delta/4$;
$r_5=r_1+\delta/8$,
$r_6=r_2+\delta/8$;
$r_7=r_1+3\delta/8$,
$r_8=r_2+3\delta/8$;
$r_9=r_1+\delta/16$,
$r_{10}=r_2+\delta/16$;
$r_{11}=r_1+3\delta/16$,
$r_{12}=r_2+3\delta/16$;
$r_{13}=r_1+5\delta/16$,
$r_{14}=r_2+5\delta/16$;
$r_{15}=r_1+7\delta/16$,
$r_{16}=r_2+7\delta/16$;

and so on, or repeating the above cycle.

By this way, the roughness on the ablated surface will not increase significantly no matter how many layers are scanned.

In the application of photo-refractive surgeries, the ablated depth profile should have a certain curve. This curve can be obtained by having different scanning area and shape for different layers. The computer 50 can be programmed to produce this curve.

The above figures and description are intended for illustrating the present invention. It is understood that various modifications can be made without departing from the scopes of the invention as defined in the appended claims.

What is claimed is:

1. A method for scanning a pulsed laser beam for uniform surface ablation comprising the steps of:
   providing a laser source producing a pulsed laser beam having a predetermined laser wavelength, pulse energy, pulse duration, and a high repetition rate;
   inserting an optical assembly into a laser beam path to obtain and control a small spot size of said laser beam on a target surface;
   providing a two-dimensional scanner receiving said laser beam and scanning said laser beam on said target at a scanning rate;
   providing a computer interfaced with said scanner to control the scanning of said laser beam in a programmable fashion so as to produce a scanning pattern of a series of smooth, close circular loops on a layer without synchronization between laser pulses and scanner positions and without predetermining pulse positions on the target;
   controlling a scanning speed of said laser beam along each close circular loop so that consecutive laser pulses are uniformly separated in each scan on said target and that a plurality of successive scans are carried out on each close circular loop, wherein the scanning speed for a circular loop of a perimeter of P for a given pulse repetition rate K is $mPK/(nm+1)$, where n is a number of laser pulses in each scan and m is a number of said plurality of successive scans on each close circular loop; and
   scanning said laser beam smoothly from loop to loop and then from layer to layer according to said scanning pattern so that the smoothness of the ablated surface remains substantially unchanged as the number of layers increases.

2. A method as defined in claim 1 wherein said providing a laser source includes providing a laser source operated at a repetition rate ranging from about 0.2 kHz to about 10 kHz.

3. A method as defined in claim 1 wherein said providing a laser source includes providing a laser source operated in the spectral range of ultraviolet, visible, and infrared.

4. A method as defined in claim 1 wherein said providing a laser source includes providing a laser source operated in the spectrum of deep UV ranging from about 220 nm to about 180 nm.

5. A method as defined in claim 1 wherein said providing a laser source includes in particular providing a laser source operated at a wavelength of about 3 microns.

6. A method as defined in claim 1 wherein said providing a laser source includes providing a laser source operated at pulse energy in the range approximately from 40 uJ to 1000 uJ.

7. A method as defined in claim 1 wherein said providing a laser source includes providing a laser source operated at pulse duration in the range approximately from 0.1 ns to 10 ns.

8. A method as defined in claim 1 wherein said inserting an optical assembly includes inserting a focusing lens.

9. A method as defined in claim 1 wherein said providing a two-dimensional scanner includes providing a pair of Galvanometers.

10. A method as defined in claim 1 wherein said inserting an optical assembly includes inserting an optical assembly into said laser beam path to obtain and control a spot size ranging from 50 to 1000 microns on the target surface.

11. A method as defined in claim 1 wherein said selecting a scanning pattern includes selecting a scanning pattern that consists of a series of concentric rings on each layer.

12. A method as defined in claim 1 wherein two consecutive pulses are spaced from each other on the target by a distance to reduce an effect of a plume produced by one pulse on the ablation of the target by another pulse.

13. A method as defined in claim 1 wherein scanning of said laser beam from loop to loop is spirally inward and outward alternately.

14. A method as defined in claim 1 wherein scanning of said laser beam layer by layer displaces peaks and valleys ablated on the target from one layer to another successive layer so as to control the radial average over the layers.

15. The method as in claim 1, wherein the scanning rate in scanning said laser beam is higher than said high repetition rate.

16. The method as in claim 1, further comprising:
maintaining the scanning speed at a constant for scanning in different loops; and
adjusting the pulse repetition rate in response to a change in the loop perimeter when scanning the laser beam from one loop to another loop.

17. The method as in claim 1, further comprising:
maintaining the pulse repetition rate at a constant for scanning in different loops; and
adjusting the scanning speed in response to a change in the loop perimeter when scanning the laser beam from one loop to another loop.

18. An apparatus for scanning a pulsed laser beam for uniform surface ablation comprising:

A laser source producing a pulsed laser beam having a predetermined laser wavelength, pulse energy, pulse duration, and a high repetition rate;

An optical assembly inserted into a laser beam path to obtain and control a small spot size of said laser beam on a target surface;

A two-dimensional scanner receiving said laser beam and scanning said laser beam on said target at a scanning rate; and A computer interfaced with said scanner to control scanning of said laser beam in a programmable fashion so as to produce a scanning pattern of a series of smooth, close circular loops of varying perimeters on a layer without synchronization between laser pulses and scanner positions and without predetermining pulse positions on the target, wherein said computer is programmed to control said scanner so that a plurality of successive scans are carried out on each close circular loop, and the scanning speed for a circular loop of a perimeter of P for a given pulse repetition rate K of said laser is mPK/(nm+1), where n is a number of laser pulses in each scan and m is a number of said plurality of successive scans on each close circular loop.

19. The apparatus as in claim 18, wherein said computer is operable to control the scanning of said laser beam layer by layer to displace peaks and valleys ablated on the target from one layer to another successive layer so as to control a radial average over the layers.

20. The apparatus as in claim 18, wherein said pulse repetition rate K is maintained at a constant, and wherein said computer is programmed to control said scanning speed when switching from scanning in one loop to scanning in another loop.

21. The apparatus as in claim 18, wherein the scanning rate in scanning said laser beam is higher than said high repetition rate.

* * * * *